US006238891B1

(12) United States Patent
Maiorella et al.

(10) Patent No.: US 6,238,891 B1
(45) Date of Patent: May 29, 2001

(54) METHOD OF INCREASING PRODUCT EXPRESSION THROUGH SOLUTE STRESS

(75) Inventors: Brian Maiorella; Duane Inlow, both of Oakland; William Howarth, Richmond, all of CA (US)

(73) Assignee: Cetus Oncology Corporation, Emeryville, CA (US)

( * ) Notice: Subject to any disclaimer, the term of this patent is extended or adjusted under 35 U.S.C. 154(b) by 0 days.

(21) Appl. No.: 08/482,421

(22) Filed: Jun. 7, 1995

Related U.S. Application Data

(63) Continuation of application No. 07/841,906, filed on Feb. 26, 1992, now abandoned, which is a continuation of application No. 07/443,445, filed on Nov. 29, 1989, now abandoned, which is a continuation-in-part of application No. 07/122,015, filed on Nov. 18, 1987, now abandoned.

(51) Int. Cl.$^7$ ............................... C12P 21/08; C12N 5/16
(52) U.S. Cl. .................... 435/70.21; 435/69.1; 435/70.1; 435/240.1; 435/240.2; 435/240.27; 435/240.3; 435/240.31; 435/252.3; 435/240.21; 435/240.26; 435/172.1; 435/172.2; 935/5; 530/412; 530/386; 530/388.1; 530/388.15
(58) Field of Search .................................. 435/69.1, 70.1, 435/70.21, 240.1, 240.2, 240.27, 240.3, 240.31, 252.3, 240.21, 240.26; 530/412, 386, 388.1, 388.15; 935/95

(56) References Cited

U.S. PATENT DOCUMENTS

| | | | |
|---|---|---|---|
| 3,926,737 | * 12/1975 | Wilson et al. | 435/3 |
| 3,937,654 | * 2/1976 | Solomons et al. | 426/60 |
| 4,724,206 | * 2/1988 | Rupp et al. | 435/69.1 |
| 5,156,964 | * 10/1992 | Inlow et al. | 435/172.1 |

FOREIGN PATENT DOCUMENTS

0101273 * 2/1984 (EP) .

OTHER PUBLICATIONS

Derwent Biotechnol. Abstracts, vol. 10, p. 83. abstract 91–14291.*
Bassett et al. 1966 in: *Principles of Chemistry*. Prentice–Hall Inc. Englewood, N.J. p. 218.*
Sienko et al. 1966 in: *Chemistry: Principles and Properties*. McGraw–Hill Book Co., New York, p. 174.*
Freshney, R. I. 1983. *Culture of Animal Cells. A Manual of Basic Technique*. Alan R. Liss, Inc. New York, p. 68.*
Reuveny et al. 1986 J. Immunol. Meth. 86, 53–59.*
*Webster's II New Riverside University Dictionary*, p. 688. (New Riverside Publ. Co. 1984).*
Lydersen, B(ed) 1987. in: *Large Scale Cell Culture Technology*. Hanser Publishers. New York. pp. 21–58.*
Pedersen et al. 1987. Ann. N.Y. Acad. Sci. 506, 163–170.*
Arathoon et al. 1986. Science. 232, 1390–1395.*
Glacken et al. 1986. Biotechnol. & Bioeng. XXVIII pp. 1376–1389.*

* cited by examiner

Primary Examiner—Christopher S. F. Low
(74) Attorney, Agent, or Firm—Philip L. McGarrigle; Paul B. Savereide; Robert P. Blackburn (57) ABSTRACT

A method of determining the optimal level of product expression and cell growth of animal cell culture is described. The method generally comprises culturing cells under conditions of solute stress, that is, under conditions whereby optimal cell growth or growth rate is decreased yet levels of product expression are increased. In a preferred embodiment of the invention is described a method of increasing the yield of monoclonal antibodies comprising culturing hybridoma cells in an environment of solute stress. One approach to the creation of such an environment is the addition of inorganic salts, organic polyols, or metabolic products to the culture medium. One- to three-fold increases in antibody yield have been obtained by these methods.

21 Claims, 3 Drawing Sheets

METHOD OF INCREASING PRODUCT EXPRESSION THROUGH SOLUTE STRESS

This application is a continuation of application Ser. No. 07/841,906, filed Feb. 26, 1992, now abandoned, which is a continuation of Ser. No. 07/443,445, filed Nov. 29, 1989, now abandoned, which is a continuation in part of U.S. patent application Ser. No. 07/122,015 filed Nov. 18, 1987, now abandoned.

FIELD OF THE INVENTION

The present invention is in the general field of biochemical engineering. More specifically, this invention is in the field of cell and tissue culture dealing primarily with somatic hybrid cell culture.

BACKGROUND OF THE INVENTION

With the advent of hybridoma technology and the accompanying availability of monoclonal antibodies, the application of such antibodies has escalated into a variety of areas of the biological sciences. For example, monoclonal antibodies have been used for the study of cell surface antigens, for affinity purification of proteins, for histocompatibility testing, for studying various viruses and for radioimmunoassay. More recently, it has been recognized that monoclonal antibodies may have medical application for drug targeting and immunotherapy (Poynton, C. H., and Reading, C. L. (1984) *Exp Biol* 44:13–33). With the increased application of the antibodies in the biological and medicinal sciences, there has come a concomitant demand for high levels of antibody production.

To date, efforts have been undertaken to develop culture conditions to maximize cell culture growth and thereby increase resultant product yield. Early work in the development of chemically defined animal cell culture media focused on the formulation of such media to achieve rapid cell proliferation (White, P. R. (1946) *Growth* 10:231–289, and Waymouth, C. (1974) *J. Natl Cancer Inst* 53:1443–1448). Such media incorporate specific nutrients, especially amino acids, vitamins, purines, and pyrimidines. Today some of the more widely used basal media for mammalian cell cultures include Hams F-12, Dulbecco's modified Eagle's medium (DME), RPMI 1640, and Iscove's modified DME. All of these above-referenced basal media are also supplemented with several trace metals and salts, including the major cations (potassium, sodium, calcium, magnesium and the like) with concentration values near isotonic levels. The role of inorganic nutrition in cell culture is discussed in a number of references including Shooter, R. A., and Gey, G. O. (1952) *Br J Exp Pathol* 31:98–103; Waymouth, C. (1974) supra; Birch, J. R., and Pirt, S. J. (1971) *J Cell Sci* 8:693–700; Ham, R. G., Growth of Cells in Hormonally Defined Media, Cold Spring Harbor Conferences on Cell Proliferation, Vol. 9, Sato, Pardee and Sirbashin, eds., 1982.

Culture media have been developed specifically for low serum and serum-free mammalian cell cultures for production of monoclonal antibodies. One such serum-free medium is disclosed in European Patent Publication 076,647, published Apr. 13, 1983. Other media have been developed by changing levels of supplements such as trace elements, vitamin and hormone additives wherein variations in the traditional basal media are slight. References to such media include, for example, Barnes, D., and Sato, G. (1980) *Cell* 22:649–655; Cleveland, W. L., et al (1983) *J Immunol Meth* 56:221–234; Iscove, N., and Melchers, F. (1978) J Ex Med 114:923–933; Kawamoto, T., et al (1983) *Analytical Biochemistry* 130:445–453; Kovar, J., and Franek, F. (1984) *Immunology Letters* 7:339–345; Murakami, H., et al (1983) *Agric Biol Chem* 47(8):1835–1840; Murakami, H., et al (1982) *Proc Natl Acad Sci USA* 79:1158–1162; Muzik, H., et al (1982) In Vitro 18:515–524; and Wolpe, S. D., "In Vitro Immunization and Growth of Hybridomas in Serum-Free Medium", in J. P. Mather, ed., *Mammalian Cell Culture*, Plenum Press, New York, 1984.

In addition to providing the right kinds and amounts of nutrients, the culture medium must also provide suitable physicochemical conditions. Parameters that are important for clonal growth of hybridoma cell culture include osmolality, pH buffering, carbon dioxide tension, and partial pressure of oxygen. These all must be adjusted to optimal values for multiplication of each type of cell with, preferably, minimal or no amounts of serum and minimal amounts of protein. Other physical factors such as temperature and illumination must also be controlled carefully.

Efforts to increase antibody yield have focused primarily on means to optimize cell growth and cell density. The optimal conditions for cell growth of mammalian cell culture are generally within narrow ranges for each of the parameters discussed above. For example, typical culture conditions for mammalian hybridoma cell culture use a basal culture medium supplemented with nutritional additives, pH in the range of 6.8 to 7.4 at 35–37C.

As a general point of reference, antibody titers from murine hybridoma cell lines are highly variable from cell line to cell line and range typically from 10 to 350 ug/ml (Lambert, K. J., et al (1987) *Dev Indust Microbiol* 27:101–106). Human monoclonal antibody expression from human/human or human/mouse fusions are also highly variable from cell line to cell line and range typically from 0.1 to 25 ug/ml (Hubbard, R., *Topics in Enzyme and Fermentation Biotechnology*, chap. 7, pp. 196–263, Wiseman, A., ed, John Wiley & Sons, New York, 1983). These values are indicative of culture conditions that are optimized for cell growth and cell viability.

Another example from the literature documents that, at least for some cell lines, monoclonal antibody production proceeds even after a culture stops growing (Velez, D., et al., (1986) *J Imm Methods* 86:45–52; Reuveny, S., et al., (1986) ibid at p. 53–59). Thus, one strategy for increasing monoclonal antibody yield has been to develop culture conditions that allow growth of hybridomas to higher cell densities and to recover the antibodies late in the stationary phase of cell culture. Arathoon, W., and Birch, J. (1986) *Science* 232:1390–1395 reported that a 1,000 liter hybridoma fermentation produced about 80 grams of monoclonal antibody during the growth phase and another 170 grams of antibody during an extended stationary/death phase. It was not reported the means, if any, by which the stationary phase of growth was extended.

Another approach from the literature to increasing antibody production is to achieve high cell densities by cell recycle or entrapment methods. Examples of these methods include hollow fiber reactors (Altshuler, G. L., et al (1986) *Biotechnol Bioeng* XXVIII, 646–658); static maintenance reactors C(Feder, J., et al, EPA 83870128.2, published Nov, 17, 1984); ceramic matrix reactors (Marcipar, A., et al (1983) *Annals N.Y. Acad Sci* 413:416–420); bead immobilized reactors (Nilsson, K., et al (1983) *Nature* 302:629–630); perfusion reactors (Feder, J., and Tolbert, W. R. (1985) *American Biotechnol Laboratory* III:24–36); and others. In some cases, a "resting" cell culture state is reported to be achieved by reducing levels of nutrients in the medium (as by reducing serum or protein supplement levels) with antibody production continuing while growth is slowed.

While a variety of methods to increase antibody yield from hybridoma cell culture are being explored, the primary focus is still on the optimization of cell growth. We have discovered that culture conditions for growth optimization and for optimal product expression may differ and that product expression can be increased under conditions of solute stress, created by the addition of certain solutes, notwithstanding the resulting growth inhibitory effects.

The concept of subjecting animal cells, especially mammalian cell cultures, to an environment of solute stress to produce higher product expression yields, such as increased antibody titers, has not been reported. One means for introducing such an environment to the culture is through salt addition which is easily monitored by measuring the osmolality of the culture medium.

Media osmolality for mammalian cell culture is usually held in the range of 280300 (Jakoby, W. B., and Pastan, I. H., *Methods in Enzymology*, vol. LVIII, "Cell Culture", Academic Press (1979), pp. 136–137). Of course, the optimal value may depend upon the specific cell type. For example, as reported in *Tissue Culture, Methods and Applications*, edited by Kruse, Jr., P. F. and Patterson, Jr., M. K., Academic Press (1973) p. 704, human lymphocytes survive best at low (about 230 mOsmol/kg), and granulocytes at higher osmolalities (about 330 mOsmo/kg). Mouse and rabbit eggs develop optimally in vivo at around 270 mOsmol/kg, 250–280 mOsmol/kg being satisfactory, while above 280 mOsmol/kg development is retarded. Iscove reports 280 mOsmol/kg to be optimum for growth of murine lymphocytes and hemopoietic cells, and Iscoves modified DME is adjusted for this growth promoting osmolality (Iscove, N. N. (1984) *Method for Serum-Free Culture of Neuronal and Lymphoid Cells*, pp. 169–185, Alan R. Liss, ed., New York.

The spread of quality control osmolality values on a number of commercially available tissue culture media is provided in a table beginning at page 706 in the *Tissue Culture, Methods and Applications* reference, supra. The osmolality values given therein reflect the 280–300 range used for mammalian cell culture.

Another means to introduce an environment of solute stress in the cell culture is through the addition of cellular metabolic products, such as lactic acid and ammonia These products are generally known to be growth inhibitory agents and strategies to reduce the level of these products in the culture medium in order to enhance cell growth have been reported. Imamura, T., et al (1982) *Analytical Biochemistry* 124:353–358; Leibovitz, A. (1963) *Am J Hyg* 78:173–180; Reuveny, S., et al. (1986) *J Immunological Methods* 86:53–59; Thorpe, J. S., et al (1987) "The Effect of Waste Products of Cellular Metabolism on Growth and Protein Synthesis in a Mouse Hybridoma Cell Line", Paper #147 presented at American Chemical Society National Meeting, Aug. 30–Sep. 5, 1987, New Orleans, La.—Symposium on Nutrition and Metabolic Regulation in Animal Cell Culture Scale-Up; and Glacken, M. W., et al (1986) *Biotechnology & Bioengineering* XXVII:137–1389.

Contrary to the teaching in the art which cautions against major adjustments to culture media osmolality and other physicochemical parameters, we have found that introducing an environment of solute stress during fermentation can favor an increase in specific (per cell) antibody expression and/or increased culture longevity which can result in an increase in antibody titer. It is to such a concept that this invention is directed. Briefly, in a preferred embodiment of the invention, an approach to mammalian cell culture which further optimizes yield of antibody production has been developed in which hybridoma cells are cultured under conditions of controlled solute stress. Optionally, the method incorporates prior art advances including the culture of hybrid mammalian cell lines in serum-flee media or in high density culture to reduce costs and facilitate purification.

SUMMARY OF THE INVENTION

Therefore, this invention is directed to a method of determining the optimal level of product expression in animal cell culture wherein the concentration of a solute of interest in a culture medium composition for optimal product expression is different than the culture medium composition determined for optimal cell growth, which method comprises:

a) growing the animal cell culture in medium to determine optimal cell growth;

b) varying the concentration of the solute in the culture medium to a concentration above that optimal for cell growth which concentration is effective to create an environment of solute stress on the cell culture;

c) monitoring the product expression under the varying solute concentrations to determine optimal product expression; and d) selecting the solute concentration that provides the optimal combination of cell growth and product expression which allows for optimal productivity.

In another aspect of this invention is provided a method of increasing the production of monoclonal antibodies during cell culture comprising culturing hybridoma cells under controlled solute stress conditions.

A preferred method of this invention comprises culturing IgM-producing hybridoma cells.

Another preferred method of this invention comprises culturing hybridoma cells which produce IgG.

These and other objects of the invention will be apparent from the following description and claims. Other embodiments of the invention embodying the same or equivalent principles may be used and substitutions may be made as desired by those skilled in the art without departing form the present invention and the purview of the appended claims.

The invention described herein draws on previous work, including scientific papers, patents, and pending patent applications. All of these publications and applications as cited previously and below are hereby incorporated by reference in their entireties.

DESCRIPTION OF THE PREFERRED EMBODIMENTS

As used herein the term "hybridoma" refers to a hybrid cell line produced by the fusion of two or more cell lines to produce an immortal cell line producing a desired product (such as an antibody). The term includes hybrids produced by the fusion of a myeloma cell line and an antibody producing cell (such as a splenocyte or plasma cell). The term also includes progeny of heterohybrid myeloma fusions (e.g., the result of a fusion with human B cells and a murine myeloma cell line) subsequently fused with a plasma cell, referred to in the art as trioma cell lines.

As used herein the term "animal" refers to any vertebrate or invertebrate species.

"Mammalian" indicates any mammalian species, and includes rabbits, rodents (e.g., rats, hamsters and mice), dogs, cats, primates and humans, preferably humans.

As used herein the term "solute" indicates a water soluble agent, including but not limited to inorganic salts and the corresponding ions thereof; organic polyols, including polypropylene glycol, glycerol and sugars such as, for example, glucose, mannose, fructose and mannitol; and metabolic products such as, for example, lactate or ammonia; which is effective in producing increased product expression.

As used herein the term "solute stress" refers to the addition of solutes in such concentrations, at least above that concentration determined for optimal cell growth, that produce a growth inhibitory effect or reduced final cell density, that is, a growth rate or maximum cell density less than that determined for optimal growth. However, the level of product expressed at this reduced growth level is comparatively greater than that level of expression achieved at the optimal growth rate owing to an increase in specific (per cell) product expression rate or an increase in longevity of the culture.

As used herein the term "osmolality" refers to the total osmotic activity contributed by ions and non-ionized molecules to a media solution. Osmolality, like molality, relates to weight of solvent (mOsmol/kg H2O) while osmolarity, like molaxity, relates to volume (mOsM/liter solution). Osmolality is one method used to monitor solute stress. Standard osmolality refers to the optimum range of clonal growth of mammalian cells which occurs at 290±30 mOsmol/kg.

In a preferred embodiment of the invention, methods have been developed for the high level production of mammalian, preferably human or murine, monoclonal antibodies for use as diagnostic reagents or for use in human therapy. In particular, a method of determining the optimal level of product expression in mammalian cell culture has been developed wherein the concentration of a solute of interest in a culture medium composition for optimal product expression is different than the culture medium composition determined for optimal cell growth, which method comprises:

a) growing the mammalian cell culture in medium to determine optimal cell growth;
  b) varying the concentration of the solute in the culture medium to a concentration above that optimal for cell growth which concentration is effective to create an environment of solute stress on the cell culture;
  c) monitoring the product expression under the varying solute concentrations to determine optimal product expression; and
  d) selecting the solute concentration that provides the optimal combination of cell growth and product expression which allows for optimal productivity.

Following the methodology set forth herein, one is able to determine the solute concentration that provides the optimal combination of cell growth and product expression for any particular cell line of interest. Once the solute concentration has been determined, one is able to create an environment of controlled solute stress for culturing the mammalian cell lines and thereby stimulate specific (per cell) product expression and/or increase culture longevity, notwithstanding the inhibitory growth effect on the cultured cells.

The mammalian cell culture used in the present invention includes, but is not limited to, any of a number of cell lines of both B-cell and T-cell origin, including murine thymic lymphoma cells, murine myeloma cells lines, murine plasmacytoma cell lines, murine hybridoma, human myeloma cell lines, human plasmacytoma cell lines, and human lymphoblastoid cells and hybridomas. Accordingly, the product to be optimized includes growth factors, lymphokines, and monoclonal antibodies. The cell cultures may include cell lines which are found to naturally produce such desired products, or have been manipulated by genetic engineering techniques to produce recombinant products.

Solute stress is introduced into the cell culture fermentation by the addition of one or more solutes which effectively inhibit optimal cell growth. The solute can be added at various time periods during the fermentation including prior to, during or after the addition of cells. While such changes to the culture media negatively affect the growth of cultured cells (given the narrow growth parameters known for optimal cell growth) the present invention lies in the discovery that culturing cells in such an environment of solute stress can positively impact specific cell productivity and culture longevity, thereby increasing product yield.

Solute stress which is effective in increasing the product yield can be achieved by increasing the concentration of a solute already present in a culture medium or introducing a new solute to the medium.

In the method of the invention, a sub-lethal solute concentration range is first determined in order to study the solute inhibitory growth effect This determination is necessary as each cell line may have unique tolerance levels to the selected solute. As a second step, various sub-lethal concentrations are studied in more detail to establish the conditions for optimal cell productivity which is responsible for increased product expression. From the data thus generated, one may determine the solute concentration that provides for the optimal combination of cell growth and product expression.

The following discussion, concerning the various types of solutes that may be used in the methods of the present invention, also provides a number of preferred concentration ranges that have been determined for specific hybridoma cell lines. Other cell lines may have somewhat different tolerance levels. These ranges are provided as a guide for determining the optimal combination of growth and product expression levels for a variety of cultured cells and are not to be construed as a limitation of the invention. The concentration ranges provided herein are a good indicator of a possible concentration range for the specific cell line of interest.

The solutes of the invention comprise a number of inorganic salts and ions thereof, including, for example, sodium chloride, potassium chloride, calcium chloride, magnesium chloride and the like, and combinations thereof. Preferred salts include sodium chloride and combinations of sodium chloride and potassium chloride. An effective concentration range for the increased production of monoclonal antibodies by the cell lines D-234 and T-88, using salts such as sodium chloride is 340 to 460 mOsmol/kg, with 350 to 400 mOsmol/kg being more preferred for the cell line D234 and 400 to 450 mOsmol/kg being more preferred for the cell line T-88. An effective concentration for the increased per cell productivity of monoclonal antibodies by the cell line 454A12, using sodium chloride, is about 400 mOsmol/kg.

The concentration values given above, as well as all concentration ranges provided herein regardless of the method of solute concentration measurement used, have been established prior to the addition of cells. However, the solute may be added before, during or after cell addition. The timing of the solute addition is generally not critical, as it has been found that increasing solute stress by, for example, salt addition, may be performed at various time points during the exponential phase of the growth cycle to achieve an increase in antibody yield. Of course, one skilled in the art will appreciate that the concentration of the metabolic solutes will increase during the course of the fermentation.

In addition to the aforementioned salts, it has been found that solutes which are generally believed to have inhibitory growth effects may also be used in the present invention. For example, lactic acid, a major metabolic end product of glycolysis in hybridoma cell culture, participates in the lowering of the pH during growth, producing sub-optimal growth conditions. The lactate ion itself, may also be growth inhibitory. Efforts have been made to reduce lactic acid production by replacing glucose with alternative sugars (i.e., fructose and galactose) that are less easily metabolized to lactate. It has been assumed that reduction of the level of lactate in the culture medium would enhance both cell growth and antibody production.

However, the present invention demonstrates that the presence of lactate during fermentation can effectively increase antibody yield notwithstanding its inhibitory growth effects. Using the methodology of the present invention, a sub-lethal concentration range (0 to 100 mM sodium lactate) was first determined in order to study the lactate inhibition effect. Various sub-lethal concentrations of sodium lactate are subsequently tested for the effect on product expression. For the cell line D-234, an effective concentration range for sodium lactate is 40 to 60 mM.

Ammonia is another substance that has concerned cell culturists due to its negative effects on cell growth. It is produced by cellular metabolism of amino acids as well as by spontaneous decomposition of glutamine. It has been assumed that reduction of ammonia in hybridoma cultures would benefit both cell growth and antibody production. However, as demonstrated herein, an increase in antibody titer was observed despite the inhibition of cell growth in the presence of ammonium chloride. For the cell line D-234, a preferred concentration range for ammonia chloride addition is 3 to 20 mM, with 10–15 mM being more preferred.

The organic polyols useful in the invention include glycerol, polypropylene glycol (PPG) and a variety of low molecular weight sugars including, for example, glucose, mannose, fructose and mannitol. Of these organic polyols, glucose is preferred, and for the cell line D-234, an effective concentration range for glucose is 6 to 20 g/l, with 7 to 15 g/l being preferred. Another preferred organic polyol is polypropylene glycol. For the cell line 454A12, an effective concentration of polypropylene glycol is about 8 $\mu$l/L.

The method of the invention is operable with any of a variety of well-known and/or commercially available mammalian cell culture media. Such suitable culture media includes serum-free media such as HL-1 (Ventrex Labs, Portland, Me.), HB104 Dana Biologicals, Berkeley, Calif.), Iscove's DME medium (Gibco, Grand Island, N.Y.) and RPMI-1640 medium (Gibco) or media supplemented with serum. The hybridomas used in the present method are preferably adapted for growth and maintenance in serum-free medium for large-scale, reproducible spinner culture production of monoclonal antibodies using, for example, the step-wise method described in U.S. Ser. No. 057,763, filed Jun. 3, 1987, entitled "Gram-Negative Bacterial Endotoxin Blocking Monoclonal Antibodies", by James W. Larrick et al., assigned to Cetus Corporation, the description of which is incorporated herein by reference.

The method of the invention has been shown to increase antibody titer regardless of the presence or absence of serum in the medium. The cell lines used in the present invention may be cell lines of diverse mammalian origin. Rat, mouse, hamster, primate and human embodiments are contemplated, with human and murine embodiments illustrated in the examples which follow. The antibodies may be of any class with IgM and IgG types being specifically exemplified herein. The human embodiments specifically exemplified herein are the products of triomas synthesized by somatic cell hybridization using a mouse x human parent hybrid cell line and Epstein-Barr virus (EBV)-transformed human peripheral blood lymphocytes (PBLs) or splenocytes from non-immunized volunteers or volunteers immunized with available Gram-negative bacterial vaccines or inactivated Gram-negative bacteria Fresh PBLs or splenocytes (not transformed) may be used, if desired. A detailed description of the synthesis of the hybridomas, including the fusion protocol, ELISAs and hybrid screening procedure, exemplified in the following examples is disclosed in U.S. Ser. No. 057,763, supra. The discussion of these procedures is incorporated herein by reference.

Briefly, the mouse-human heterohybrid fusion partner designated F3B6 was constructed by fusing human PBL B cells obtained from a blood bank with the murine plasmacytoma cell line NS1 obtained from the American Type Culture Collection (ATCC) under ATCC No. TIB18 (P3/NS1/1-AG4-1). The resulting hybrid cells were adapted for growth in 99% serum-free medium and deposited with the ATCC under ATCC No. HB-8785.

The heterohybrid F3B6 cells and positive EBV-transformed PBL B cells were then used to construct hybridoma cells lines which secrete antibodies illustrative for use in the method of the present invention. A preferred strategy for preparing and identifying such hybrids follows. Cells (PBLs, splenocytes, etc.) are panned on cell-wall lipopolysaccharide (LPS) (an endotoxin of a gram-negative bacteria which produces bacteremia) coated tissue culture plates, then EBV transformed and fused to the tumor fusion partner (mouse myeloma x human B cell or rat myeloma). Panning involves incubation of the population of immunocompetent cells on a plastic surface coated with the relevant antigen. Antigen-specific cells adhere.

Following removal of non-adherent cells, a population of cells specifically enriched for the antigen used is obtained. These cells are transformed by EBV and cultured at approximately $10^3$ cells per microtiter well using an irradiated lymphoblastoid feeder cell layer. Supernatants from the resulting lymphoblastoid cells are screened by ELISA against an *E. coli* Rc LPS and a Salmonella Re LPS. Cells that are positive for either Rc or Re lipid A LPS are expanded and fused to a 6thioguanine-resistant mouse x human B cell fusion partner. If the mouse x human B cell fusion partner is used, hybrids are selected in ouabain and azaserine. Supernatants from the Rc or Re positive hybrids are assayed by ELISA against a spectrum of Gram-negative bacteria and purified Gram-negative bacterial LPSs. Cultures exhibiting a wide range of activity are chosen for in vivo LPS neutralizing activity. Many but not all antibodies so produced are of the IgM class and most demonstrate binding to a wide range of purified lipid A's or rough LPS's. The antibodies demonstrate binding to various smooth LPS's and to a range of clinical bacterial isolates by ELISA.

Two of the hybridoma cell lines which produce the Gram-negative bacterial endotoxin blocking antibodies described above were used to illustrate the methods of the present invention. D-234 and T-88 are representative of hybridomas used in the methods of the present invention to produce increased yields of their respective monoclonal antibodies. D-234 was adapted to growth and maintenance in serum-free medium for large-scale production of monoclonal antibodies. The D-234 hybridoma was created from a fusion of the heterohybrid fusion partner F3B6 and human B lymphocytes; a hybridoma sample adapted for growth in serum-free media was deposited with the ATCC under accession number HB-8598. The T-88 hybridoma is a fusion product of the same heterohybrid F3B6 and human splenocytes from a lymphoma patient. A sample of this hybridoma (that was not adapted for growth in serum-free media) was deposited with the ATCC under accession number HB-9431. In addition, a subsequent hybridoma passage of D234 was deposited with the ATCC under accession number HB-9543. These latter two hybridoma cell lines are specifically exemplified in the following examples.

The murine-murine hybridoma cell line, 454A12, used as an example here was formed from the fusion of a mouse splenocyte and a mouse myeloma fusion cell partner. This hybridoma produces IgG monoclonal antibodies specific for human transferrin receptor. The 454A12 hybridoma, its production, and the antibody it produced were described in U.S. patent application Ser. No. 069,867, "Anti-human Ovarian Cancer Immunotoxins and Methods of Use Thereof", filed Jul. 6, 1987, applicants Bjorn, M. J. et al.

The following examples are illustrative of this invention. They are not intended to be limiting upon the scope thereof.

EXAMPLE 1

Culture of D-234

A one ml ampule of frozen D-234 stock (ATCC SIB-9543) was thawed quickly in a 37° C. water bath. The contents were aseptically added to 100 ml prewarmed, pregassed (95% air and 5% $CO_2$), serum-free HL-1 medium (Ventrex Labs, Portland, Me.) supplemented with 0.1% Pluronic polyol F-68 and 8 mM L-glutamine in a 250 ml Erlenmyer flask with a loosely fitted plastic screw cap. The flask was placed in a humidified incubator (36.5° C., 90% relative humidity and 5% $CO_2$) and cultured with shaking at 100–120 rpm.

This parent culture was subcultured during mid-exponential phase, about 2–4 days after inoculation, when the cell density was approximately $5 \times 10^5$ to $1 \times 10^6$ viable cells per ml. The subcultures were grown in the daughter flasks under the same culture conditions as above, starting with the initial inoculum of $1 \times 10^5$ and $5 \times 10^4$ viable cells/ml. The cells were counted using a Coulter Counter, and viability was determined by trypan blue exclusion using an hemocytometer. Maximum total cell densities were around 1.7 million with viable cell densities around 1 million.

For standard batch production, the cultures were allowed to grow to completion which occurs about 7 to 10 days from planting by which time cell viability had declined to 30% or less. The cells were harvested by centrifugation (3,000 rpm for 5 min) to separate the cells and purify the antibodies.

The resulting antibody yield was determined by enzyme-linked immunoabsorbent assay (ELISA) using a standard IgM ELISA but modified by using a high salt (i.e., at least 0.5 M NaCl) assay buffer. IgM titers were around 40 ug/ml.

EXAMPLE 2

Effect of Salt Addition on IgM Production In D-234

Figure 1A:
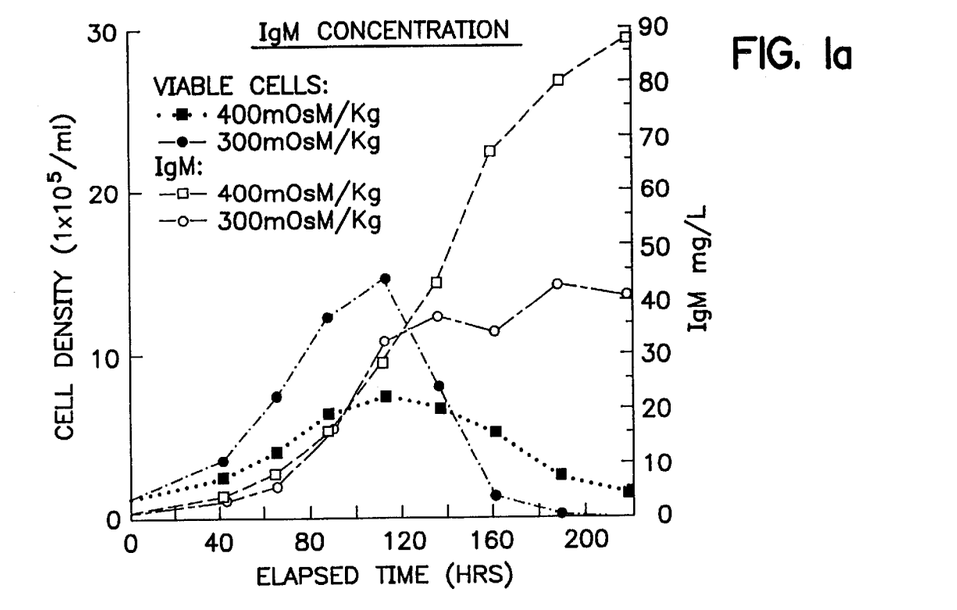
FIG. 1 shows the effect of 400 mOsmol/kg media on antibody yields of human/human/murine trioma D-234 cells in serum-flee HL-1 media. The closed circles represent cell growth in 300 mOsmol/kg media and the open circles represent the resulting IgM antibody yield. The closed squares represent cell growth in 400 mOsmol/kg media and the open squares represent resulting IgM antibody yield.
Figure 1B:
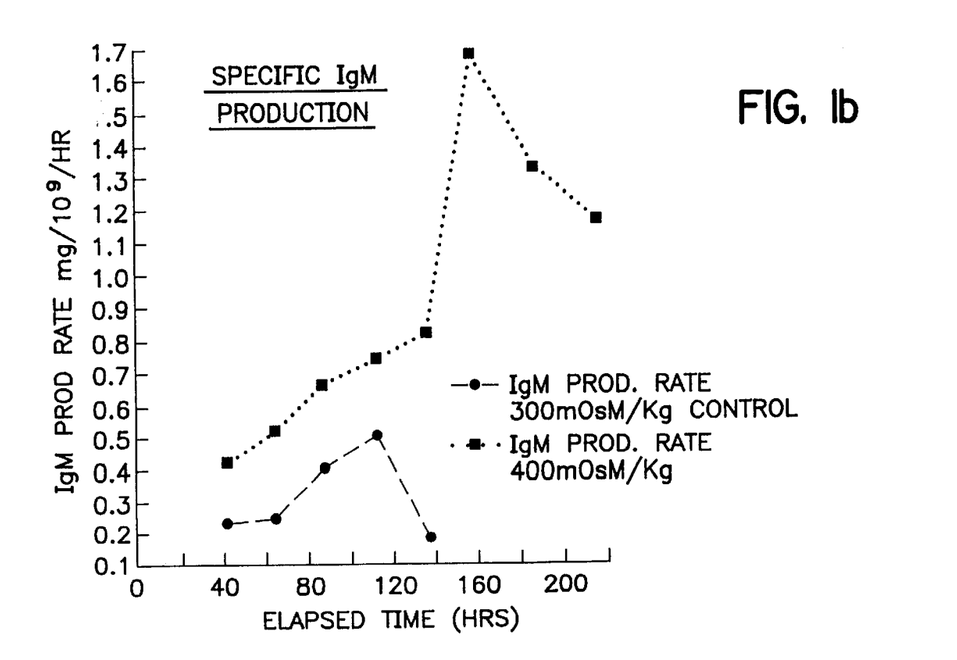

The following treatments were set up in 100 ml working volume shake flasks at standard planting densities in HL-1 with 0.1% pluronic F-68 and 8 mM glutamine. A 3.75 M salt solution (27:1 molar ratio NaCl:KCl) was used to increase salt concentration beyond that of the standard HL-1 medium Approximately $1 \times 10^5$ viable cells/ml were used to inoculate the aforementioned culture medium, which was used as the control sample. In addition, $1 \times 10^5$ viable cells/ml were inoculated into a 400 mOsmol/kg initial osmolality medium. A third sample was formed by inoculating the standard osmolality medium and, after 88 hours of culture, the 3.75 M salt solution was added to a final concentration of 400 mOsmol/kg. At this time point, the cell density was determined indicating that the culture contained ~$1.2 \times 10^6$ vc/ml. The cells in each of the three cultures were cultured for 9 days, during which time the cell viability and cell density levels were monitored. The IgM titers were determined for each of the three experimental runs. The results of these experimental runs are provided in FIG. 1 and in Table 1 below. As indicated therein, a twofold increase in final IgM titers over the control (~90 mg/L) was correlated with prolonged viability and increased specific IgM production rates in 400 mOsmol/kg cultures where growth rate and cell density are reduced.

TABLE 1

D-234 Summary Table

| | 300 mOsmol/kg Control | 400 mOsmol/kg Initial | "Add Salt" (at 88 Hours) |
|---|---|---|---|
| Maximum Total Cell Density ($10^5$/ml) | 23 | 12 | 22 |
| Maximum Viable Cell Density ($10^5$/ml) | 15 | 7.5 | 14 |
| Ave. Exponential Growth Rate mu (1/hr) | 0.033 (0 to 66 hr) | 0.028 (0 to 89 hr) | 0.032 (0 to 89 hr) |
| Final IgM Concentration (mg/L) | 41 | 88 | 58 |
| Ave. Exponential IgM Production Rate (mg/$10^9$/hr) | 0.24 | 0.56 | 0.40 |

For the 400 mOsmol/kg initial culture, exponential growth rate "mu" and maximum cell density were reduced, which was indicative of solute stress. The duration of the culture was increased in the high osmolality culture, and the specific IgM productivity rate was twofold to threefold higher than the control. The extra IgM over and above the control was produced after the peak in viable cell density.

A 1.5-fold increase in final IgM titer to ~58 mg/L was observed in the culture where salt was added at 88 hours. Specific IgM production rates increased from one day after salt addition into the viable cell decline (versus the control, where production rate declined after the viable cell peak), even though there appeared to be little, if any, difference in the growth curve compared to the control.

For the D-234 cell line, salt addition near the peak viable cell density has an IgM production enhancing effect in the decline phase without any extension of the viable cell curve. This suggests that specific IgM production rates can be increased without slowing growth (and limiting ultimate cell densities) early in culture. However, for D-234, final titers are not as high as those achieved in slow growing (limited cell density) cultures planted in high osmolality medium.

EXAMPLE 3

Effect of Inoculation Density and Timing of Salt Addition

Using the methods described in the foregoing examples, the effects of initial inoculation density of D-234 on the specific cell productivity and timing of the salt addition were explored.

A control was run at the standard osmolality of 300 mOsmol/kg medium using cultures planted at $5\times10^4$ cells/ml. These cells exhibited good growth, but viable cell densities were lower than that produced for the cultures planted at $1\times10^5$ cells/ml (and total cell density of 1.6 versus 1.9 million) with an extension of the viable phase from six to seven days. However, final IgM titers were similar. At 370 mOsmol/kg, $5\times10^4$ cells/ml inoculated cultures resulted in significant growth slowing and lowering of viable cell density and titers, about half compared with $1\times10_5$ planted cultures.

Various solute stress conditions were tested using the $5\times10^4$ inoculation density culture. Titers for 300, 340 and 370 cultures were 40, 75, and 35 mg/L, respectively. It was found that adding salt at day one instead of at day zero to the 370 mOsmol/kg allowed the $5\times10^4$ culture to reach viable cell densities ($5\times10^5$ cells/ml) and a titer (65 mg/L IgM) approaching the $1\times10^5$, 370 culture values ($6\times10^5$ cells/ml and 75 mg/L IgM).

From the results of the previous experiment, 340 and 370 mOsmol/kg were chosen as osmolalities to test with salt added on day 0, 1, 2, or 3. The results indicated that adding salt at different times to the 370 mOsmol/kg culture resulted in a slight increase (60 to 65 mg/L final IgM) in final titer concentration.

For the 340 mOsmol/kg culture, the addition of salt at day 1 and day 2 led to higher titers (~110 mg/L) than did day 3 addition (~90 mg/L) or day 0 (~70 mg/L).

EXAMPLE 4

Effect of Salt Addition on T-88 Growth and IgM Production

T-88 cells were grown in replicate 100 ml working volume shake flasks of HL-1 media with 0.1% w/v Pluronic polyol F8, 8 nM glutamine and 5% added fetal calf serum at 300 mOsmol/kg (control); 340 mOsmol/kg, 400 mOsmol/kg; and 450 mOsmol/kg. Like the above examples, osmolality was increased by the addition of a 3.75 M salt solution with a 27:1 molar ratio NaCl:KCl. The cultures were grown for 7 days, during which time the cell density and cell viability were periodically monitor Complete growth curves were generated for the control and for the 400 mOsmol/kg flasks. The 400 mOsmol/kg growth curve showed slow growth and reduced cell density, therefore indicating solute stress had occurred The duration of the culture was extended, during which IgM production over and above the control was obtained. The specific IgM production rate was higher at 400 mOsmol/kg over most of the culture period. Table 2 shown below, illustrates that a 30% reduction in total cell density and a 20 to 25% increase in final IgM titer for the 400 and 450 mOsmol/kg shake flasks was achieved. IgM produced per million cells from day three to day four was about two times higher at 400 and 450 mOsmol/kg compared with the control and 340 mOsmol/kg treatment. Exponential phase doubling time (Td) for the 400 mOsmol/kg treated flasks was higher than for the control (27 versus 20 hours).

TABLE 2

T-88 + 5% FCS Summary Table

| | Control | | | |
|---|---|---|---|---|
| | 300 mOsmol/kg | 340 mOsmol/kg | 400 mOsmol/kg | 450 mOsmol/kg |
| Maximum Total Cell Density ($10^5$/ml) | 23 | 24 | 17 | 17 |
| Final IgM Concentration (mg/L) | 37 | 35 | 43 | 46 |
| IgM Produced per Million Cells From Day 3 to Day 4 (ug/$10^6$ cells/day) | 6 | 7 | 15 | 11 |
| Ave. Exponential Growth Rate mu (1/hr) | 0.037 (Td 20) | | 0.034 (Td 27) | |

EXAMPLE 5

Effect of Lactate on D-234 Growth and IgM Production

This example describes the effect of sodium lactate on growth, viability, and IgM production of D-234.

Approximately $1\times10^5$ cells/rn of D-234 were grown in 250 ml shake flasks (agitated at 100 rpm) in HL-1 medium containing 0.1% Pluronic polyol F-68 and 8 mM glutamine. A 1 M stock solution of sodium lactate (pH 7.4) in HL-1 was added to the medium. A preliminary screen of the effect of a broad range of sodium lactate concentrations (0–100 mM) on D-234 growth and IgM production was run. It was determined that growth was greatly inhibited by levels of added lactate above 40 mM. Cell densities at day four were reduced at all levels of lactate tested with a critical drop between 40 and 60 mM.

The results of this experiment are given in Table 3 below.

TABLE 3

Effect of Na Lactate on D-234 Growth, and IgM Production

| Initial Lactate | Total Cell Density $1 \times 10^5$/ml (% Viability) | | IgM ug/ml | |
|---|---|---|---|---|
| mM | Day 2 | Day 4 | Day 4 | Day 7 |
| 0 | 4.7 (95) | 21.0 (90) | 10 | 24 |
| 20 | 5.6 (96) | 15.0 (92) | 20 | 35 |
| 40 | 5.1 (92) | 12.9 (89) | 22 | 54 |
| 60 | 2.2 (93) | 4.1 (87) | 19 | 61 |
| 80 | 2.1 (81) | 2.6 (65) | 15 | 28 |
| 100 | 2.2 (72) | 2.0 (50) | 11 | 14 |

The results indicate that the production of IgM by D-234 was increased with increasing concentrations of sodium lactate up to 60 mM where growth was extremely inhibited, and IgM production peaked at 61 ug/mil compared to the control at 24 ug/ml. Even at 80 mM added lactate, the level of IgM produced was similar to that seen for the control, even though the cell density was only 12% of the control. Specific (per cell) productivity was increased up to 14-fold (at 60 mM added lactate).

EXAMPLE 6

Effect of $NH_4Cl$ on D-234 Growth and IgM Production

The hybridoma D234 was grown in HL-1 serum-free medium supplemented with 0.1% Pluronic polyol F-68, 10 mM glutamine and 10 mM $NH_4Cl$. A control was also run without $NH_4Cl$. One hundred ml cultures in 250 ml shake flasks were inoculated at an initial density of $1\times10^5$ viable cells/ml (91% viability).

Figure 2:
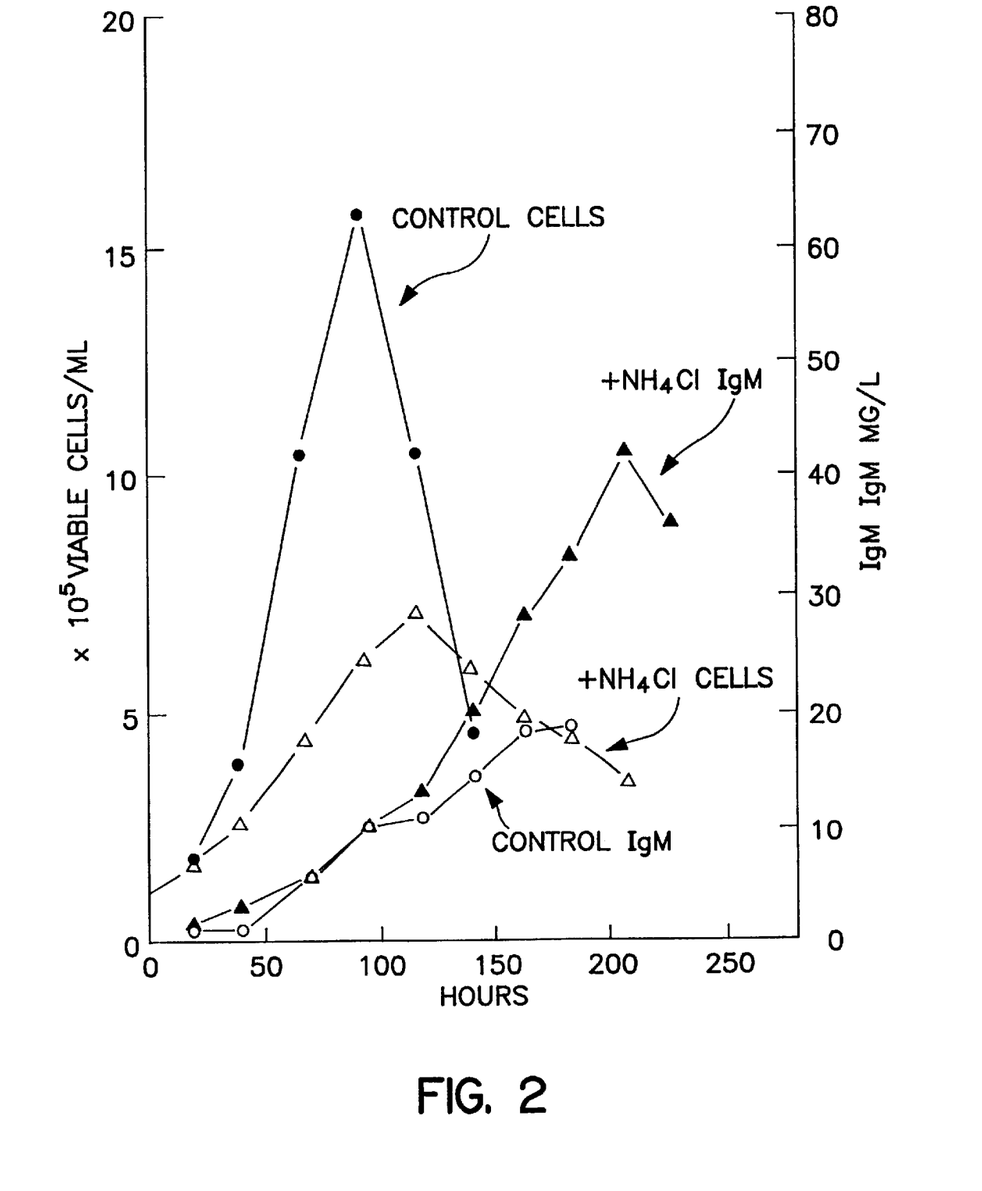
FIG. 2 shows the effect of ammonium chloride on production of antibodies of D-234 cells. The closed circles represent cell growth in the absence of ammonium chloride and the open circles represent the resulting IgM antibody yield. The open triangles represent cell growth in the presence of 10 mM ammonium chloride and the closed triangles represent resulting antibody yield.

As illustrated in FIG. 2, the addition of 10 mM $NH_4Cl$ inhibited the growth, reduced both viability and the maximum total cell density of the culture ($2.3\times10_6$/ml for the control vs $1.1\times10^6$/ml when 10 mM $NH_4Cl$ was added). However, this stress condition prolonged the stationary/decline phase and resulted in a 2-fold increase in the production of IgM.

EXAMPLE 7

Effect of High Glucose Concentration on Antibody Production

The hybridoma D-234 was grown in HL-1 medium (Ventrex) which already contains 5.5 g/l. A 500 g/l stock solution of glucose was used to increase the glucose level of the HL-1 medium. The total glucose levels tested in this example were 5.5 (control), 10.5, 15.5, and 25.5 g/l.

The 10.5 g/l glucose culture grew more slowly than the control and began to die sooner. While the control reached a maximum of $8.7\times10^5$ viable cells/ml, the 10.5 g/l stressed culture reached $7.1\times10^5$ viable cells/ml. However, the death phase of this culture was longer than the control resulting in higher antibody production: 85 verses 67 mg/l.

The 15.5 g/l glucose culture proved to be very stressful for D-234 resulting in a low maximum viable cell density ($4.3\times10^5$ viable cells/ml) and producing IgM at 50 mg/l. The 25.5 g/l glucose condition proved to be lethal.

EXAMPLE 8

Effect of Polypropylene Glycol on IgG Production

The following experiment showed that when polypropylene glycol (PPG) was added to hybridoma 454A12 cell culture, it increased the IgG production of the hybridoma by 40%. Though PPG limited the maximum cell density achievable by the culture, it slowed the decline in culture viability after the peak density had been attained.

The hybridoma 454A12 was grown in 125 ml shake flasks filled to 50 ml with HL-1 and 4 mM glutamine. The test sample contained 8 $\mu$L of polypropylene glycol whereas the control was without the PPG.

It was observed that the test sample exhibited an exponential phase growth rate similar to the control at 0.054 hour$^{-1}$. However, the test sample experienced a lag in growth of one day, and a higher exponential phase death rate of 0.0059 hr$^{-1}$. Additionally, the test sample had a lower maximum cell density than the control. The test sample reached a maximum cell density of only 1.3 million cells/ml, where the control reached a maximum cell density of 2 million cells/mil.

Beyond the maximum cell density peak, the decline in cell viability in the test sample was slower than in the control. The test sample yielded a final IgG concentration of 63 $\mu$g/ml, which was about 40% higher than the control, which yielded 46 $\mu$g/ml of IgG.

EXAMPLE 9

Effect of Sodium Chloride on IgG Production

Figure 3:
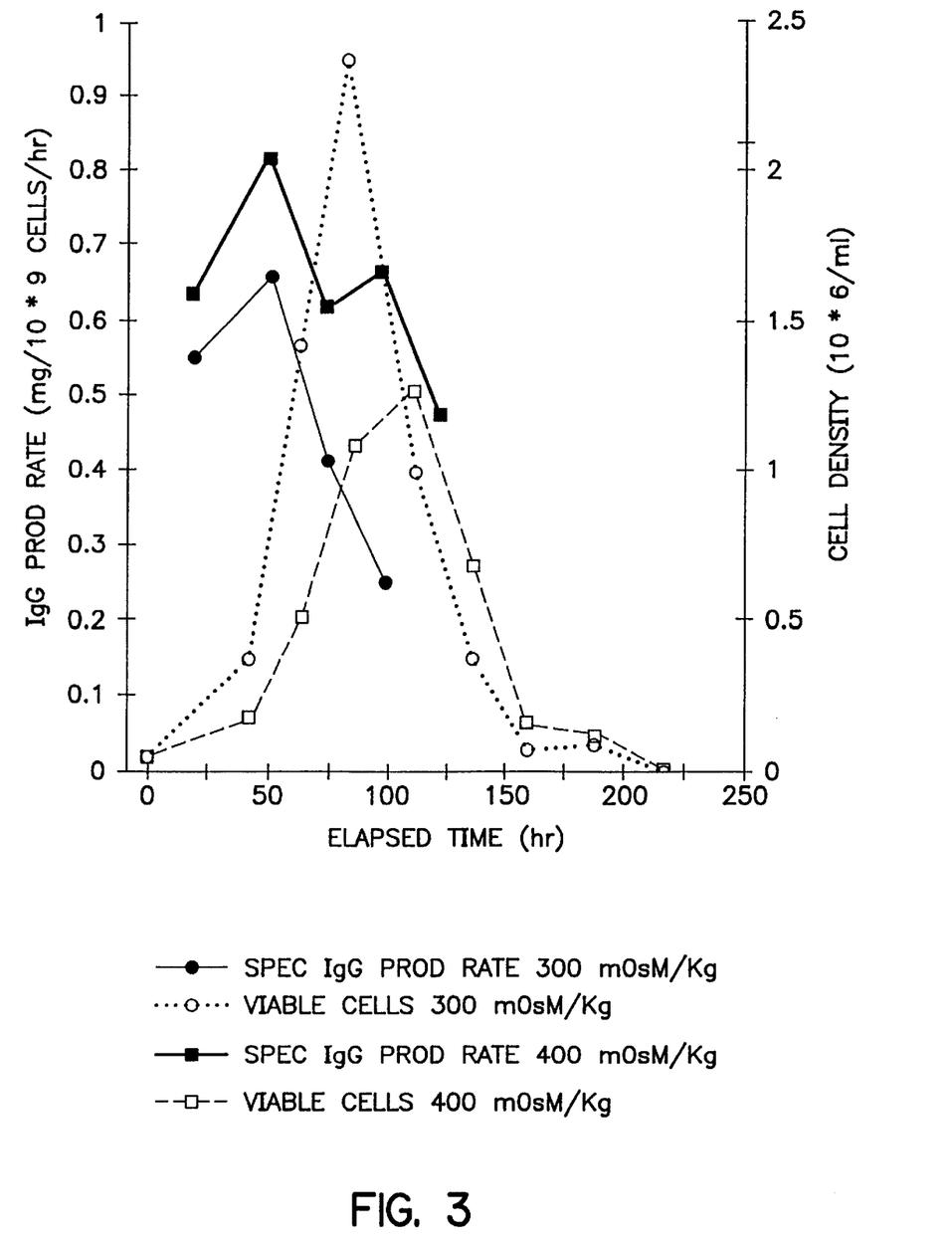
FIG. 3 shows the effect of sodium chloride on specific production rate of IgG antibody by hybridoma 454A12.

In another experiment, the 454A12 hybridomas were grown in shake flasks with commercially available HL-1 medium (Ventrex) supplemented with 8 mM glutamine. Osmolality of the standard (control) HL-1 medium was 300 mOsmol/kg. In the test sample, the osmolality was increased to 400 mOsmol/kg using sodium chloride. The result of solute stress in the test sample was evidenced by a 50% decrease in maximum cell density. In the stressed condition, the specific IgG production rate per cell increased throughout the culture period. The increase in specific productivity was greatest during the post exponential phase period of the culture when specific productivity was more than 60% higher under the stressed condition (FIG. 3).

Deposition of Cultures

The hybridomas used in the above examples, except for 454A12, to illustrate the method of the present invention were deposited in and accepted by the American Type Culture Collection (ATCC), 12301 Parklawn Drive, Rockville, Md., USA, under the terms of the Budapest Treaty. In addition, the mouse x human fusion partner F3B6 adapted to 99% serum-free medium which partner was the source of these hybridomas was similarly deposited with the ATCC. The deposit dates and the accession numbers are given below:

| Culture | Deposit Date | Accession No. |
|---|---|---|
| D-234 | Aug. 10, 1984 | HB-8598 |
| D-234 | Sep. 17, 1987 | HB-9543 |
| T-88 | May 19, 1987 | HB-9431 |
| F3B6 | Apr. 18, 1985 | HB-8785 |

Samples of the 454A12 hybridomas had been deposited with In Vitro International, Inc., (formerly at 7885 Jackson Road, Suite 4, Ann Arbor, Mich. 48103, U.S.A., currently at 611 P. Hammonds Ferry Road, Linthicum, Md. 21090, U.S.A., telephone number (301) 789–3636) on Jun. 18, 1985, under the Accession No. IVI10075. This deposit was made under the Budapest Treaty and will be maintained and made accessible according to the provisions thereof.

Availability of the deposited cell lines are not to be construed as a license to practice the invention in contravention of the rights granted under the authority of any government in accordance with its patent laws.

Also, the present invention is not to be considered limited in scope by the deposited hybridomas, since they are intended only to be illustrative of particular aspects of the invention. Any animal cell line (including any hybridoma) which can be used for production of protein according to the methods described in this patent application is considered within the scope of this invention. Further, various modifications of the invention in addition to those shown and described herein apparent to those skilled in the art from the preceding description are considered to fall within the scope of the appended claims.

We claim:

1. A method for increasing expression of a protein in a mammalian cell culture in aqueous medium, which already provides for all cell growth requirements, and recovering the protein from the culture, wherein the expression is increased above the expression level at optimal growth, comprising adding to the cell medium at least one solute selected to inhibit cell growth or density when present in said cell culture at a concentration above the concentration which is optimal for cell growth where the solute increases the stress on the cells in the absence of prior adaptation of the cells to the increased solute stress; and recovering and purifying protein from the cell culture, wherein the protein had been expressed while subjected to such stress.

2. A method in accordance with claim 1, wherein the solute is selected from the group consisting of sodium chloride, potassium chloride, calcium chloride, magnesium chloride, sodium lactate, ammonia, glycerol, polypropylene glycol, glucose, mannose, fructose and mannitol.

3. A method in accordance with claim 1, wherein the mammalian cell culture is a hybridoma selected from the group consisting of D-234 (ATCC HB-8598), D-234 (ATCC HB-9543), T-88 (ATCC HB-9431), and 454A12 (IVI 10075).

4. A method in accordance with claim 2, wherein the mammalian cell culture is composed of D-234 cells and the osmolality of the medium with the addition of sodium chloride is in the range of 350 to 400 mOsmol/kg.

5. A method in accordance with claim 2, wherein the mammalian cell culture is composed of T-88 cells and the osmolality of the medium with the addition of sodium chloride is in the range of 400 to 450 mosmol/kg.

6. A method in accordance with claim 2, wherein the mammalian cell culture is comprised of 454A12 hybridomas, and the osmolality of the medium with the addition of sodium chloride is about 400 mOsmol/kg.

7. A method in accordance with claim 2, wherein the sodium lactate concentration is in the range of 40 to 60 mM.

8. A method in accordance with claim 2, wherein ammonia is added as ammonium chloride and the ammonium chloride concentration is in the range of 3 to 20 mM.

9. A method in accordance with claim 8, wherein the ammonium chloride concentration is in the range of 10–14 mM.

10. A method in accordance with claim 2, wherein the polypropylene glycol concentration is 8 $\mu$l/L.

11. A method in accordance with claim 2, wherein the glucose concentration is in the range of 7–15 g/L.

12. A method to determine a solute concentration in a cell culture medium to produce the highest protein product expression from a cell, the culture medium has all the requirements necessary for optimal growth, said method comprising: determining the concentration of the solute necessary for optimal cell growth; increasing the concentration of the solute to a concentration above that optimal for cell growth to place the cell under increased solute stress, wherein the solute is selected to be capable of inhibiting cell culture growth at elevated concentrations; and determining the concentration which provides increased protein product expression in the absence of prior adaptation of the cells to the increased solute stress.

13. A method in accordance with claim 1, wherein the solute is selected from the group consisting of inorganic salts and the corresponding ions thereof, organic polyols, and metabolic products.

14. A method in accordance with claim 1, wherein the protein is an antibody.

15. A method for recovering antibodies from hybridoma cells grown in a growth medium, said method comprising growing said cells in the growth medium in the presence of at least one solute which is selected from the group consisting of sodium chloride. potassium chlorides calcium chloride, magnesium chloride, sodium lactate, ammonia or its ions, glycerol, polypropylene glycol, glucose, mannose, fructose, and mannitol, and which is present at a concentration sufficient to increase the solute stress upon the cells so as to inhibit cell growth or density and enhance expression of the antibody in the cells in the absence of prior adaptation of the cells to the increased solute stress; and recovering the antibody from the growth medium containing the solute.

16. A method as in claim 15, wherein the antibody is a monoclonal antibody.

17. A method as in claim 16, wherein the solute is sodium lactate present at a concentration in the range from 40 to 60 MM.

18. A method as in claim 16, wherein the solute is ammonium chloride present at a concentration in the range from 3 to 20 mM.

19. A method as in claim 16, wherein the solute is propylene glycol present at a concentration of 8 $\mu$l/L.

20. A method as in claim 16, wherein the solute is glucose present at a concentration in the range from 7 to 15 g/L.

21. A method as in claim 16, wherein the solute is sodium chloride present at a concentration in the range from 340 to 460 mOs/kg.

* * * * *